(12) United States Patent
Stauber

(10) Patent No.: US 8,545,503 B2
(45) Date of Patent: Oct. 1, 2013

(54) SURGICAL TOOL AND METHOD

(76) Inventor: Marshall Ephraim Stauber, Hollywood, FL (US)

( * ) Notice: Subject to any disclaimer, the term of this patent is extended or adjusted under 35 U.S.C. 154(b) by 440 days.

(21) Appl. No.: 12/485,519

(22) Filed: Jun. 16, 2009

(65) Prior Publication Data
US 2010/0318138 A1    Dec. 16, 2010

(51) Int. Cl.
*A61F 2/46*      (2006.01)
*A61M 5/178*    (2006.01)

(52) U.S. Cl.
USPC ................................ 606/86 R; 604/164.13

(58) Field of Classification Search
USPC .................. 606/86 A, 256; 604/528, 164.13, 604/264, 160, 154, 506
See application file for complete search history.

(56) References Cited

U.S. PATENT DOCUMENTS

2005/0216014 A1*  9/2005  May et al. ...................... 606/72
2009/0082754 A1*  3/2009  Hentrich et al. ............... 604/506

\* cited by examiner

*Primary Examiner* — Sameh Boles
(74) *Attorney, Agent, or Firm* — McHale & Slavin, P.A.

(57) ABSTRACT

A medical device and method. The medical device includes a handle portion, a shank portion, a guide channel and a flexible guide device. The shank portion has a non-linear portion adjacent a distal end. The device is useful in performing medical procedures in the pre-sacral area of a human patient. After inserting the guide device, the shank may be removed leaving the guide device in place and a second medical device can be inserted into the site of interest using the guide device for guidance. The medical procedure can be performed using the second medical device.

4 Claims, 2 Drawing Sheets

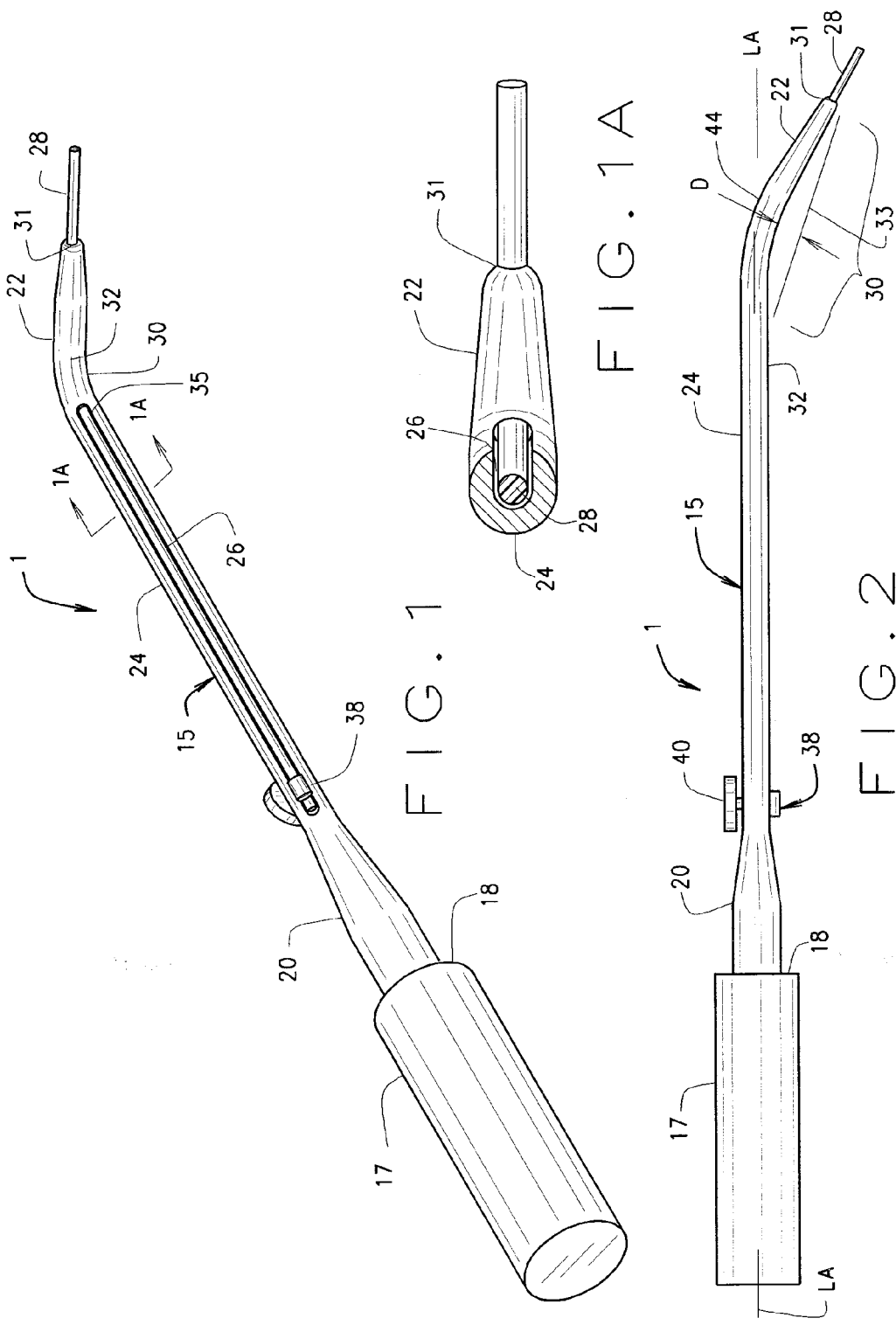

SURGICAL TOOL AND METHOD

FIELD OF INVENTION

A surgical tool and method for medical procedures in the pre-sacral area of a human patient. The tool includes a non-linear distal end portion of a shank. The shank includes a guide channel operable for directing movement of a flexible guide device. After insertion of the guide device in the patient, the shank is removed and the guide device is used to direct movement of a second shank into the surgical site for treatment.

BACKGROUND OF THE INVENTION

The pre-sacral region of the human body is difficult to access with probes such as jamshidi needles. The bowel is close to the sacrum and cannot be perforated, pinched or cut without potential adverse consequences. Additionally there is soft tissue in the area that needs to be avoided. The pre-sacral region is difficult to access with current probes because of the proximity of parietal and visceral fascia, neurovascular structures and the concave curvature of the anterior surface of the sacrum. Currently used probes are necessarily straight and enter the space occupied by the bowel and by necessity force the bowel to move away from the sacrum to form a pathway to the last lumbar making a medical treatment in the area of the last lumbar vertebra such as full end plate removal difficult to perform without risking damage to the neurovascular structures and the bowel.

There is thus a need for an improved treatment tool and method for accessing the pre-sacral area to perform medical treatments.

SUMMARY

The invention involves the provision of a medical device for use in the pre-sacral area for medical treatment in the area of the sacrum and last lumbar vertebra. The device includes an elongate shank having a distal end portion, a proximal end portion and an intermediate portion extending between the distal and proximal end portions. The shank includes a guide channel extending along at least a portion of the intermediate and proximal end portions. The channel is configured for removably receiving a guide device therein for longitudinal movement therealong. The shank has a non-linear portion located in at least one of the intermediate portion and distal end portion providing a deviation ratio of less than about 32:1. A handle is located adjacent the proximal end portion of the shank.

A flexible guide device is removably positioned in at least a portion of the guide channel.

The invention also involves the provision of a method of performing a medical procedure in the pre-sacral area. The method includes forming an opening in the skin adjacent a patient's pre-sacral area. A first shank is extended through the opening with the first shank having a non-linear portion adjacent a proximal end portion. The non-linear portion has a deviation ratio of less than about 32:1. The first shank forms a surgical passage into the pre-sacral area. A flexible guide device is inserted into the surgical passage with its movement being guided with at least a portion of a longitudinally extending guide channel in the first shank to a desired penetration depth into the surgical passage. The first shank is removed and the flexible guide device is left in the surgical passage. A second shank is inserted into the surgical passage toward a site of interest using the flexible guide device to guide movement of the second shank. The flexible guide device is removed and a medical procedure is performed utilizing the second shank.

BRIEF DESCRIPTION OF THE DRAWINGS

FIG. 1 is a perspective view of a medical device for use in the pre-sacral area of a patient.

FIG. 1A is an enlarged fragmentary view of the distal end portion of the shank of the medical device of FIG. 1.

FIG. 2 is a side elevation view of the medical device shown in FIG. 1.

Like numbers used throughout this application represent like or similar parts and/or construction.

DETAILED DESCRIPTION OF THE INVENTION

Figure 3:
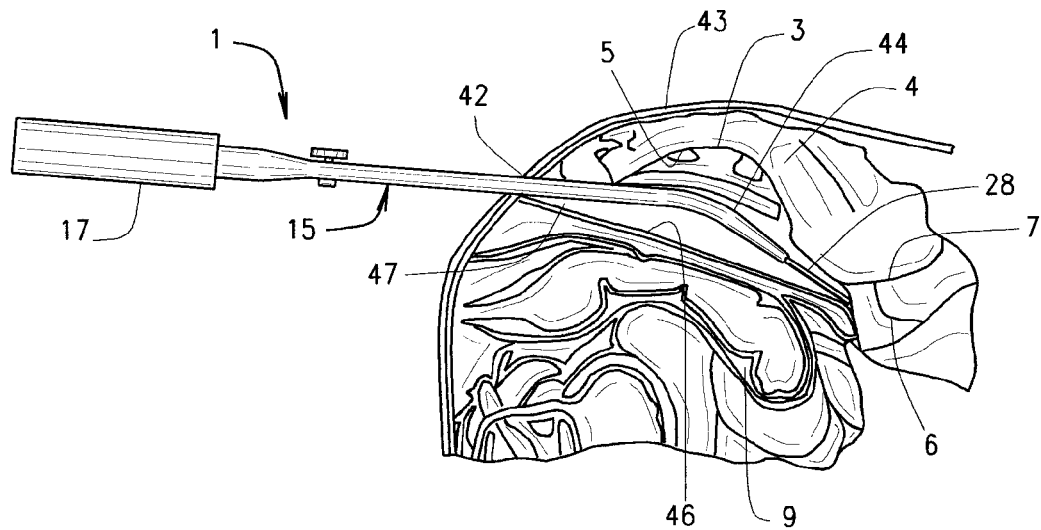
FIG. 3 is a side sectional view of the medical device inserted in a patient.
Figure 4:
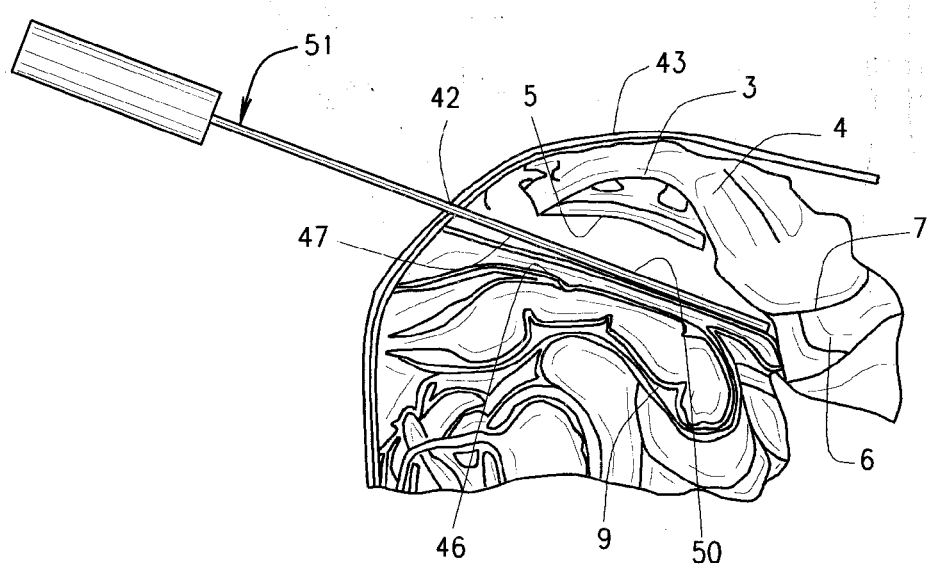
FIG. 4 is a side sectional view similar to FIG. 3 but showing a second medical device directed toward a surgical site.

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

The reference numeral 1 designates generally a medical device usable to access the pre-sacral area 3 of a human patient. The pre-sacral area 3 includes the sacrum 4 having a concave anterior surface 5. The lower lumbar vertebra 6 is located at the proximal end 7 of the sacrum 4. A portion of the lower intestine 9 is also located in the pre-sacral area 3 and is an obstacle to accessing the upper area of the pre-sacral area. The use of medical devices like a jamshidi needle can result in damage to the lower intestine which needs to be avoided. Because of the shape of the sacrum 4 and the proximity to the lower intestine 9, safe access to the lower lumbar vertebra 6 for such medical procedures as full volume discectomy and endplate removal is difficult with current tools. Current medical tools, such as a jamshidi needle with trocar pose a risk of bowel puncture or cutting during insertion with attendant problems from such injuries.

The medical device 1 includes a shank 15 and a handle 17 located at the proximal end 18 of the shank 15. The handle 17 may be attached permanently or removably to the shank 15 or may be an integral part of the shank 15. Preferably, the handle 17 is formed separately and attached to the shank 15. The shank 15 has a proximal end portion 20, a distal end portion 22 and an intermediate portion 24. Preferably, the shank 15 is of a metal alloy (herein metal for convenience) such as stainless steel and the handle 17 may be of metal or polymeric material.

The shank 15 is elongate with proximal end portion 20 and a portion of the intermediate portion 24 having a central longitudinal axis LA. It also has a guide channel 26 preferably extending along the distal end portion 22 and at least a portion of the intermediate and proximal end portions 24, 20 respectively and is configured for removably receiving a guide device 28 therein for relative longitudinal movement therealong. The guide channel 26 can be open along at least a portion of its length and is preferably enclosed along a portion of the channel located in the distal end portion 22 of the shank 15. The channel 26 opens on the distal end 31 for the guide 28 to exit from. The shank 15 has a non-linear portion 30 located in at least one of the intermediate portion 24 and distal end portion 20. The non-linear portion 30 is preferably curved providing a deviation ratio of less than about 32:1. For purposes of this invention, the deviation ratio is the ratio of the length of a portion of the shank 15 in the non-linear section 30 divided by the maximum distance D from a chord line 33. Specifically, the deviation ratio is determined by dividing a chord line 33 length of 4 inches starting at the distal end 31 and D is the maximum distance D to the inside surface 32 from the chord line 33 over the 4 inch chord length. Preferably, the deviation ratio is in the range of between about 32:1 and about 3:1 and more preferably in the range of between about 24:1 and about 5:1. It is noted that the deviation ratio also applies to the convex side of the shank 15 since the convex and concave sides are preferably generally concentric.

The guide channel 26 is operable to retain the guide 28 associated with the shank 15 during insertion of the guide 28. Preferably the guide 28 is relatively resiliently flexible and may be made from a nylon monofilament line like that used in string trimmers having a diameter of between about 1/16" and about 3/16". As shown, the guide channel 26 includes a portion 35 that has an open side opening on the concave side or inside surface 32. At the distal end portion 22, the channel is preferably closed and is in the form of a tube opening on the distal end 31. The guide device 28 is sized and shaped to be freely longitudinally movable in the channel 26. A retainer 38 may be provided to selectively fix the guide device 28 against longitudinal movement along the shank 15. As shown, the retainer 38 is in the form of a clamp with a knob 40 that will clamp the guide 28 between a portion of the retainer 38 and the shank 15.

The present invention is better understood by a description of its use in performing a medical procedure like a discectomy or end plate removal. An opening 42 is formed in the patient's skin 43 as by making an incision adjacent a patient's pre-sacral area 3. The shank 15 is inserted though the opening 42 and the concave side 32 faces generally away from the anterior surface 5. The shank 15 is positioned and moves between the sacrum 4 and the posterior portion 46 of the lower intestine 9. The convex side 44 moves along the anterior surface 5 until the distal end 31 reaches the site of interest, for example, the lower lumbar vertebra 6. The shank 15 forms a surgical passage 47 into the pre-sacral area 3. The flexible guide 28 is moved into the pre-sacral area 3 either with the shank 15 or after the shank 15 is inserted to the desired penetration depth. The guide channel 26 fixes the path of movement of the guide device 28. The device 28 is also inserted to a desired penetration depth. The shank 15 may then be removed while leaving the guide device 28 in place. After the shank 15 is removed, a second shank 50 of a tool 51, such as a jamshidi needle may be inserted through the opening 42 and moved along the guide 28 (which forms a pathway along the tissue in the pre-sacral area 3) as by having the guide 28 move through an internal passage in the shank 50. The shank 50 is moved along the surgical passage 47 with its movement being guided by the flexible guide device 28 to a desired penetration depth in the surgical passage 47. The guide device 28 may then be removed and the medical procedure performed using the second shank 50 of the tool 51. The procedure may utilize a trocar to penetrate bone or other medical implement.

It is to be understood that while certain forms of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A medical device for use in a pre-sacral area for medical treatment in an area of the sacrum and last lumbar vertebra, the device including: an elongate shank having a distal end portion, a proximal end portion and an intermediate portion extending between the distal and proximal end portions, said shank including a guide channel extending longitudinally along at least a portion of the intermediate and distal end portions and configured for removably receiving a guide device therein for longitudinal movement therealong, said guide channel in at least a portion of said distal end portion defined by a continuous wall defining a tubular shaped distal end for maintaining an enclosure about a curved portion of a guide device when inserted therein, said distal end having a terminal opening sized and shaped to provide passage there through of a guide device, wherein the guide channel having an open side along at least a portion of a length of the intermediate portion; A retainer selectively limit relative movement between the guide device and the shank, the retainer is in the form of a clamp with a knob that will clamp the guide device between a portion of the retainer and the shank, wherein the clamp being mounted on the shank; said shank having a non linear portion located in at least one of the intermediate portion and distal end portion defined by a deviation ratio for providing a passage way within the pre-sacral area; wherein the non linear portion being curved and having a convex side and a concave side, wherein the convex side and the concave side being generally concentric; a handle located adjacent the proximal end portion; and a flexible guide device removably positioned in at least a portion of the guide channel.

2. The medical device of claim 1 wherein said distal end portion providing a deviation ratio of less than about 32:1.

3. The medical device of claim 2 wherein the deviation ratio being in a range of between about 32:1 and about 3:1.

4. The medical device of claim 2 wherein the deviation ratio being in a range of between about 24:1 and about 5:1.

* * * * *